United States Patent [19]

Wurzburger

[11] Patent Number: 5,686,706

[45] Date of Patent: *Nov. 11, 1997

[54] DISPENSABLE, DISPOSABLE COVER FOR STETHOSCOPES

[75] Inventor: Isaac Wurzburger, Monsey, N.Y.

[73] Assignee: M&W Medical Supplies L.L.C., Monsey, N.Y.

[*] Notice: The portion of the term of this patent subsequent to Aug. 16, 2013, has been disclaimed.

[21] Appl. No.: 616,597

[22] Filed: Mar. 15, 1996

Related U.S. Application Data

[63] Continuation-in-part of Ser. No. 385,671, Feb. 8, 1995, Pat. No. 5,528,004, which is a continuation of Ser. No. 209,601, Mar. 10, 1994, Pat. No. 5,424,495, which is a continuation-in-part of Ser. No. 106,656, Aug. 16, 1993, abandoned.

[51] Int. Cl.⁶ ............................................. A61B 7/02
[52] U.S. Cl. .......................................... 181/131
[58] Field of Search ............................. 181/131, 137; 381/67; 128/715

[56] References Cited

U.S. PATENT DOCUMENTS

| | | | |
|---|---|---|---|
| 3,867,925 | 2/1975 | Ersek | 181/131 |
| 4,461,368 | 7/1984 | Plourde | 181/131 |
| 4,867,268 | 9/1989 | Ulert | 181/137 |

*Primary Examiner*—Khanh Dang
*Attorney, Agent, or Firm*—Gottlieb Rackman & Reisman

[57] ABSTRACT

A dispensable, disposable cover for stethoscopes prevents the transfer of disease or other contaminants through the incorporation of a shield of any geometric shape, having an adhesive backing for removably attaching the shield over the entire surface area of a diaphragm of a stethoscope. The shield is peelably detachable from the stethoscope diaphragm after use. In alternate embodiments of the cover, the shield has extending therefrom a pull-tab or a flap. In another embodiment, an annular lip sized for receipt by the stethoscope diaphragm is upraised from the cover and has the adhesive backing thereon, with the remainder of the cover having no adhesive backing and acting as the flap.

10 Claims, 4 Drawing Sheets

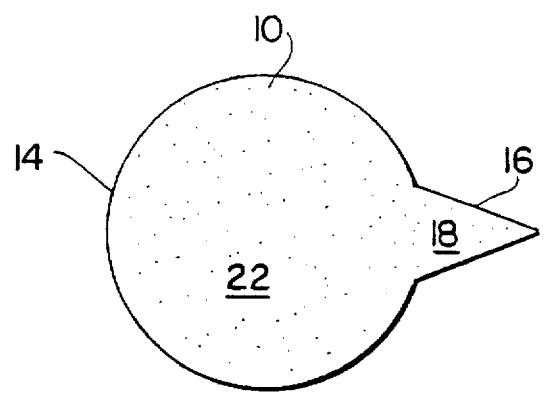
F I G. 1A
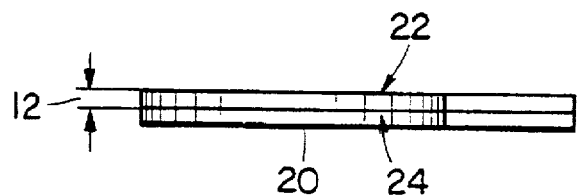
F I G. 1B
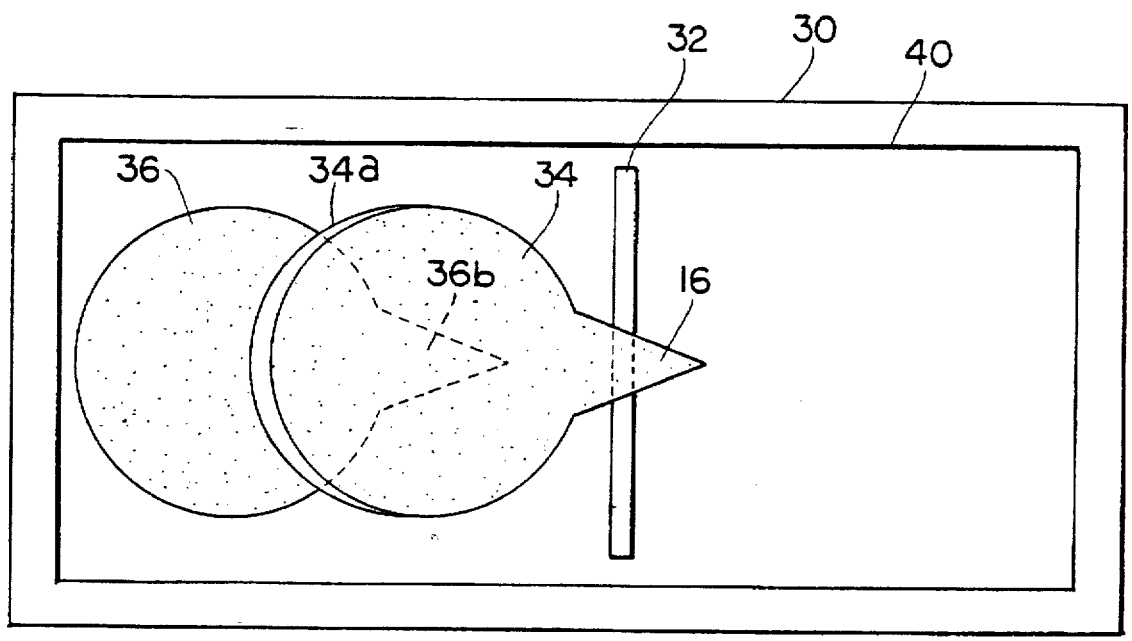
F I G. 2

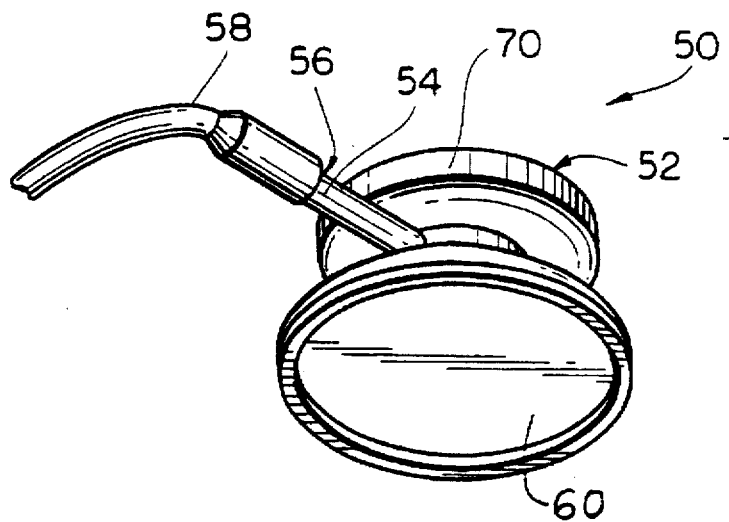
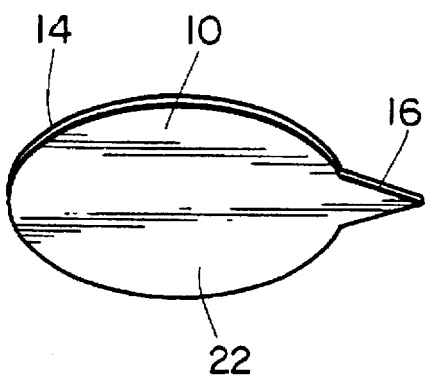
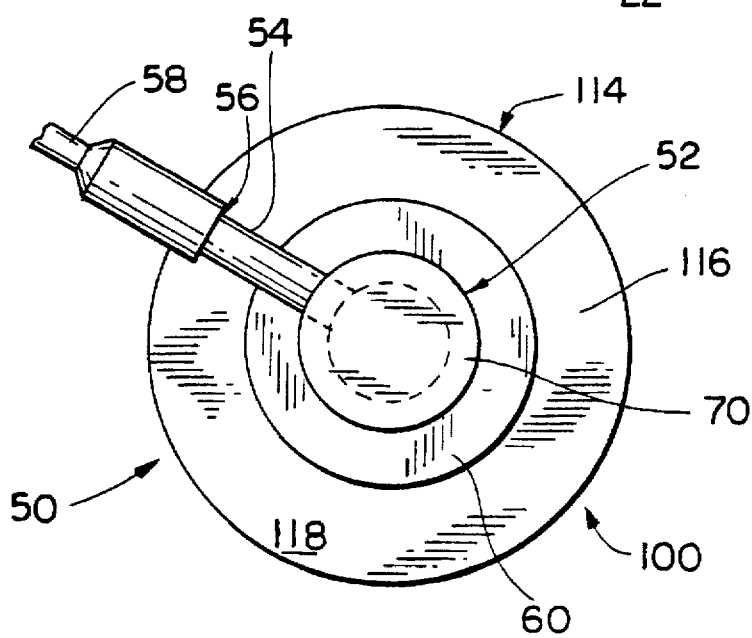
FIG.3
FIG.4

DISPENSABLE, DISPOSABLE COVER FOR STETHOSCOPES

FIELD OF THE INVENTION

This is a continuation-in-part of application Ser. No. 08/385,671, filed Feb. 8, 1995, now U.S. Pat. No. 5,528,004, which is a continuation of application Ser. No. 08/209,601, filed Mar. 10, 1994, now U.S. Pat. No. 5,424,495, which is a file wrapper continuation-in-part of application Ser. No. 08/106,656, filed Aug. 16, 1993, now abandoned.

This invention relates to medical equipment and accessories, in general, and to a cover for the diaphragm of a stethoscope which serves to provide a barrier to the passage of body fluids, hair, dirt, skin tissues and any other contaminants from a patient to the stethoscope, in particular.

BACKGROUND OF THE INVENTION

As is well known and understood, stethoscopes are used extensively in medical practice to allow a physician or other provider of medical care to monitor sounds in the respiratory, cardiac, plural, arterial, venus, and other body systems. As is also well known and understood, it is typical for physicians and other care providers to employ this highly used medical instrument from patient to patient, either by constantly having it upon their person, or near at hand, while in the treating environment. (For example, and when carried about, it is not unusual to find the physician or provider of medical care to employ the stethoscope on between 15–20 patients per hour in a hospital environment, and anywhere between 6 and 12 patients in an office setting.) As the acceptable practice, the diaphragm of the stethoscope in such usage is placed directly on the skin of the patients—and, as a result, the entire stethoscope diaphragm thus becomes susceptible to contamination and to the passing of such contamination from patient to patient unless the diaphragm is sterilized between each use. However, as such process is extremely time consuming, a sterilization of the stethoscope diaphragm is not common, even if there existed—which there does not—any recommended procedure for the sterilization of the stethoscope diaphragm.

As is also well appreciated, such danger of contamination being transferred is magnified when used in neo-natal care, where the newborns are most at risk to the transfer of communicable diseases, colds, or other contaminants. Since a stethoscope is often placed at points where such body fluids and contaminants as blood, urine, tears, exist, it becomes even more important that the stethoscope diaphragm either be sterilized between uses, or be shielded in use so as to limit the opportunity for such fluids and contaminants to reach the stethoscope diaphragm itself.

It is also desirable to protect both the patient and the physician from contacting each other near the stethoscope diaphragm in order to prevent the transfer of body fluids and other contaminants between the patient and the physician.

OBJECTS OF THE INVENTION

It is, therefore, an object of the invention to provide a disposable cover for a stethoscope which prevents the passage of body fluids and other contaminants from the patient to the diaphragm of the stethoscope.

It is also an object of the invention to provide a disposable cover for a stethoscope which prevents the passage of body fluids and other contaminants between the patient and the physician.

It is another object of the invention to provide such a disposable cover which can be easily located and identified in a care facility.

It is a further object of the invention to provide such a disposable cover which is easy to apply and remove by the care provider, and in a safe manner.

It is yet another object of the invention to provide such a disposable cover in a dispenser which is simple to manufacture and utilize, and which can easily be positioned for use at the care facility.

It is another object of the invention to provide such dispensable, disposable covers for stethoscope diaphragms which are exceedingly simple to apply in use, and to discard after use.

It is still a further object of the invention to provide such a disposable cover which is impregnated with an antimicrobial or chemical solution for killing germs.

BRIEF DESCRIPTION OF THE DRAWINGS

These and other features of the present invention will be more clearly understood from a consideration of the following description, taken in connection with the accompanying drawings, in which:

FIGS. 1A and 1B illustrate a preferred embodiment of a disposable cover embodying the principles of the invention;

FIG. 2 illustrates a type of dispenser which may be employed with the disposable cover of FIG. 1;

FIG. 3 is an exploded perspective view of a stethoscope having a diaphragm and the cover;

FIG. 4 is a top plan view of the stethoscope of FIG. 3 showing a second embodiment of the disposable cover;

DETAILED DESCRIPTION OF THE PREFERRED EMBODIMENTS

Figure 5:
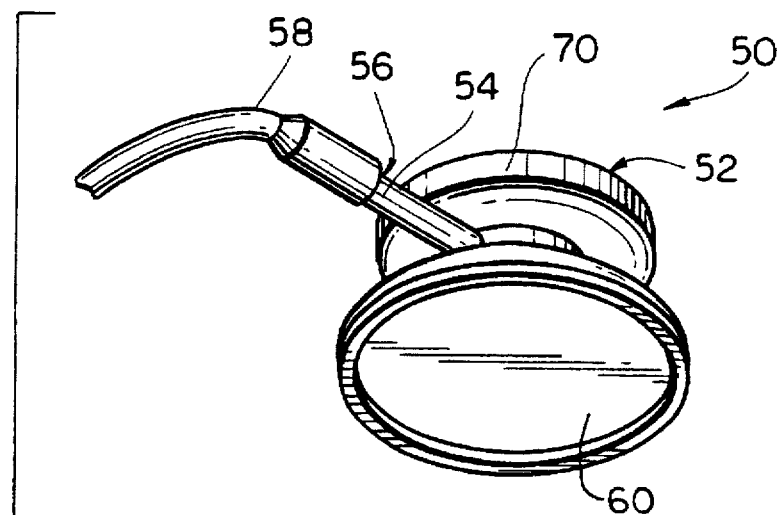
FIG. 5 is an exploded perspective view of a third embodiment of the stethoscope having a disposable cover.

As seen in FIGS. 3 and 4, a stethoscope 50 has a head 52, a diaphragm 60 and a bell chamber 70. A hollow tube 54 extends from head 52 and ends at an end 56. Attached over end 56 of tube 54 is a hose 58, which terminates at two ear plugs (not shown) for placement in the ears of a user of stethoscope 50.

The top view of FIG. 1A and the side view of FIG. 1B are helpful in an understanding that the preferred embodiment of the disposable cover of the invention is composed of a shield 10 of a plastic film material having a predetermined thickness 12 and a defined edge surface 14. A pull-tab 16 extends from the edge surface 14, as at 18, for grasping by the physician or other care provider in temporarily affixing shield 10 to diaphragm 60 of stethoscope 50 (see FIGS. 3 and 4), and for detaching and discarding shield 10 after a single patient use. To such end, shield 10 has first and second sides 22 and 24, respectively, both sides selected to have a contour to cover diaphragm 60 of stethoscope 50, wherein second side 24 is provided with an adhesive backing 20 of any appropriate composition to secure it to stethoscope diaphragm 60 so that the contour of shield 10 covers the entire surface of diaphragm 60 that touches the patient's body when stethoscope 50 is in use. The use of adhesive backing 20 allows shield 10 to be peelably detachable from diaphragm 60 after patient usage.

Turning now to FIG. 4, stethoscope 50 of FIG. 3 is shown with a second embodiment of shield 10, shown at 100. Shield 100 is substantially identical to shield 10 of FIGS. 1–3, except that instead of pull-tab 16, shield 100 has flap 116. Shield 100 has edge 114, which edge defines both the diameter of shield 100 and the circumference of shield 100 and flap 116. Specifically, flap 116 is merely an annular continuation of pull-tab 16 of shield 10. As with pull-tab 16, surface 118 of flap 116 (see FIG. 4) has no adhesive. Flap 116 accordingly achieves two major goals: (1) it is easily graspable by the physician in temporarily affixing shield 100 to diaphragm 60 of stethoscope 50, and for detaching and discarding shield 100 after a single patient use; and (2) it protects against contact between the hand of the physician and the patient's body when stethoscope 50 is used, thereby preventing transfer of body fluids and other contaminants between the patient and the physician.

Figure 6:
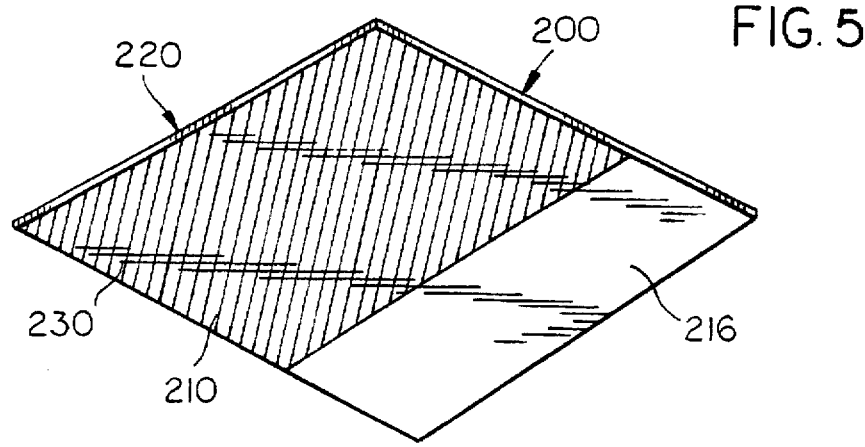
FIG. 6 is a top plan view of the stethoscope of FIG. 5 showing a fourth embodiment of the disposable cover.
Figure 6:
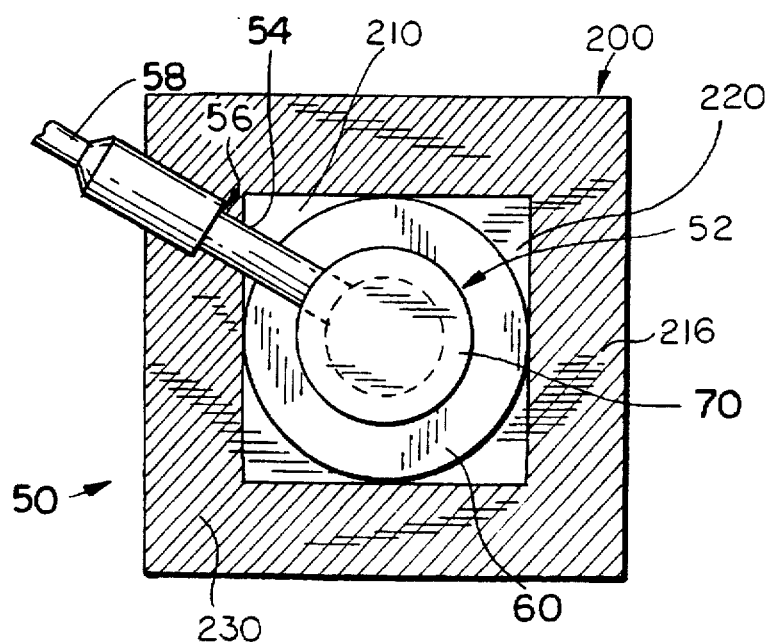

Turning now to FIGS. 5 and 6, in alternate embodiments to those of FIGS. 1–4, the shield is seen to be substantially square or rectangular in shape, and is indicated at 200. Shield 200 has a shield portion 210 having adhesive backing 220 thereon and a pull-tab or flap 216 extending therefrom. Shield 200 is used in an identical manner to shields 10 and 100, in that shield 200 is easy to handle by using pull-tab/flap 216, which has no adhesive, for attaching and removing shield 200 from a diaphragm 60 of a stethoscope 50. Specifically, adhesive backing 220 of shield 200 is selectively attachable to diaphragm 60 so that shield portion 210 fully covers diaphragm 60. Flap 216 of FIG. 6 is meant to act identically to flap 116 of FIG. 4, and to achieve the goals of flap 116.

Figure 7:
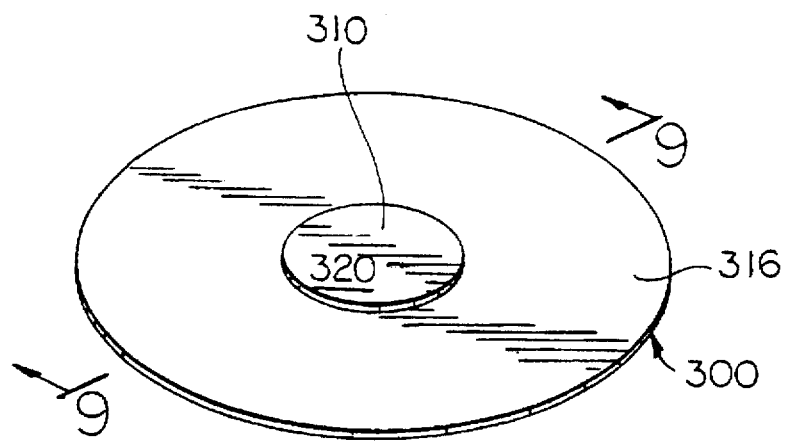
FIG. 7 is a perspective view of a fifth embodiment of the disposable cover.
Figure 8:
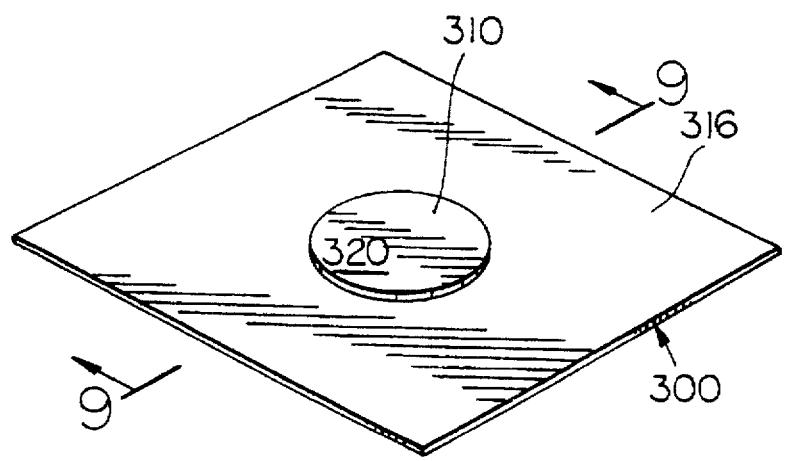
FIG. 8 is a perspective view of a sixth embodiment of the disposable over.
Figure 9:
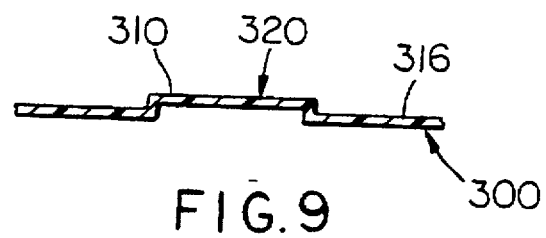
FIG. 9 is a cross-sectional view taken along line 9—9 of FIGS. 7 and 8.

Turning to FIGS. 7–9, another embodiment of the inventive cover is shown. In this embodiment, a shield 300 is shown with an upraised shield portion 310 and a surrounding flap 316. In use, shield portion 310 would be sized substantially equivalently to the size of diaphragm 60 of stethoscope 50, so as to better fit against diaphragm 60 in the case where the stethoscope head has a rim around diaphragm 60, as seen in FIG. 3. In this embodiment, an adhesive backing 320 would be situated as shown in FIGS. 7–9, preferably with no adhesive in any other location of shield 300.

Turning again to FIGS. 5 and 6, the inventive cover is also shown having coloring 230. In FIG. 5, coloring 230 is shown to be on shield portion 210, while on FIG. 6, coloring 230 is shown to be on flap 216. It is accordingly anticipated by the invention that coloring 230 may be on any portion of shield 200 (or 10, 100 or 300), including on the entire surface of the shields. As is stated below, the coloring helps to remind a physician or care provider of the presence of the cover on the stethoscope, and thereby remind that person to so remove the cover before using the stethoscope on the next patient.

It is to be noted, and specifically understood, that shields 10, 100, 200 and 300 can have any shape, be it circular, square, rectangular, or any other shape, so long as diaphragm 60 is fully covered.

Obviously, and so as not to interfere with the normal use of stethoscope 50 in allowing the monitoring of sounds in the various body systems, shields 10, 100, 200 and 300 are selected of a narrow thickness, yet sufficient to sustain use, such as 2 mils thick, in the preferred embodiments of the invention. In accordance with intended usage, the plastic film material of shields 10, 100, 200 and 300 may be manufactured to be sterile or non-sterile and packaged as such—and with the peelable adhesive backing 20, 220 or 320, could even be affixed to the patient's chart (not shown) after use as an alternative to being discarded—and in such employment, may be fabricated of a matte acetate material, so as to be written upon with pen and ink as part of the patient's treatment history chart.

As has been stated above, by further making these shields of a colored, opaque plastic film material, their presence can be most easily noted by the physician and care provider, so that their re-use for the next patient will easily be avoided to assure that any body fluids, diseases, and/or contaminants will not be transmitted. Such feature fosters the removal of the shield after use, its discarding, and its replacement by a new shield for the next patient to be seen. In utilizing the invention, it will be readily understood that the dimensions selected for the shield and its configuration depends upon intended use—and, typically, a circular configuration of some 1.5 inch diameter for the contour of shields 10 and 100 or a 1.5 inch square for shield portion 210 (i.e., the area over which adhesive backing 20, 220 or 320 is applied), will most usually suffice—although, in neo-natal care instances, a smaller diameter or side length might be employed to fit with the usually smaller stethoscope diaphragm there employed. In any event, the shield will be placed in position on the stethoscope diaphragm 60, and removed from it after use for discarding by the healthcare provider, simply by grasping onto pull-tab 16 of shield 10, flap 116 of shield 100, pull-tab/flap 216 of shield 200 or flap 316 of shield 300—which, as contradistinct from the contour of shields 10 and 100, shield portion 210 of shield 200 and shield portion 310 of shield 300, is devoid of any adhesive backing.

Another feature of the present invention is to impregnate the cover with an antimicrobial or chemical solution for killing germs.

One further feature of the present invention lies in its ready location for use—as, for example, by any appropriate securing to a wall alongside the patient bed in a healthcare facility, or alongside a patient table in an office treatment room. Alternatively, on a counter at either location, a plurality of the shields may be provided in a dispenser for serial grasping by the medical provider through the existing pull-tab 16, as illustrated by the configuration in FIG. 2, through flap 116 for shields 100 (not shown) or through pull-tab/flap 216 or 316 for shields 200 and 300 (not shown). There, a plastic dispenser 30 is shown, with a center slot 32 through which the pull-tab 16 of the first of several shields protrude. As will be appreciated, the adhesive backing 34a of first shield 34 extends to cover over pull-tab 36b of the next underlying shield 36 so as to automatically draw the shield 36 into position by pulling on pull-tab 16 when removing shield 34 from dispenser 30 for use. With a shield material thickness of some 2 mils, a dispenser providing up to 50, or even 100, shields can thus be had, in a dispenser having a thickness 40 of approximately 1 inch, or less. Pulling on the tab of an overlying shield in dispenser 30 thus automatically draws out the tab of the underlying shield immediately adjacent to it. Obviously, the dimensions of the dispenser 30 depend upon the shields to be stored therein, for use with whatever the size and shape of the stethoscope diaphragm might happen to be.

While there has been described what is considered to be preferred embodiments of the present invention, it will be readily appreciated by those skilled in the art that modifications can be made without departing from the scope of the teachings herein. Thus, whereas the preferred embodiments of the invention have been described in employing a plastic film material, preferably of matte acetate, and preferably of a circular shape, any type of composition can be employed—acetate, polyester, or otherwise—and any shape can be employed, as long as the material can be readily affixed to diaphragm 60 of stethoscope 50, can be peelably detached therefrom, and is of a density and thickness which does not interfere with the monitoring of transmitted sounds from the body systems and cavities. In similar fashion, any type of appropriate adhesive material can be utilized. For example, a synthetic that affords a sufficient amount of adhesion so as to affix to the stethoscope diaphragm when in use, while being able to be peelably detached for discarding. Additionally, depending upon the diameter of the stethoscope diaphragm, additional manufactures of dispenser 30 may be employed—even to the extent of replacing the described arrangement of positioning consecutive shields one atop of the other with an arrangement wherein the shields are adjacent one another on a continuous roll (not shown), and separated one from another by perforations (not shown) to be cut by serated edges at a slot of a different dispenser through which the plastic film material shields may be drawn. Although possible to strengthen the shield securement to the stethoscope diaphragm by employing types of "elastic bands" around the edges of the disc to exert a holding force on the stethoscope diaphragm when in position, such utilization of these "elastic holding adjuncts" are not as desirable as the arrangement of the described embodiment, and for at least the reason of their added cost and increased bulk in formulating the dispensing package. In either event, it will be appreciated that such use of the plastic film securement also serves to afford a "warmer" touch to the patient's skin than exists with the typically used stethoscope which, by necessity, picks up a cooler temperature from its surrounding room environment just by hanging around the physician's neck or by lying on a counter.

It will thus be seen that the objects set forth above, among those made apparent from the preceding description, are efficiently attained and, since certain changes may be made in the above constructions without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. For a stethoscope having a diaphragm with a surface area for touching a body of a person, a cover for said diaphragm of said stethoscope, comprising:

a shield having first and second sides, said first side for touching said body of said person; and an adhesive backing on said second side of said shield, said adhesive backing for detachably adhering said shield to said surface area of said diaphragm of said stethoscope so that said shield entirely covers said surface area of said diaphragm of said stethoscope.

2. A cover as recited in claim 1, wherein said shield has a shield portion and a pull-tab or flap extending from said shield portion.

3. A cover as recited in claim 2, wherein said shield portion or said pull tab/flap is colored for ease of viewing.

4. A cover as recited in claim 2, wherein said adhesive backing is on said shield portion.

5. A cover as recited in claim 4, wherein said pull-tab and said flap is devoid of adhesive backing.

6. A cover as recited in claim 1, wherein said shield is of the order of 2 mils thick.

7. A cover as recited in claim 1, wherein said shield is composed of matte acetate so as to accept writing thereon.

8. A cover as recited in claim 2, wherein said shield portion of said shield is upraised for receipt of said shield portion against said surface area of said diaphragm of said stethoscope.

9. In combination, a plurality of covers for a diaphragm of a stethoscope having a surface area and a dispenser for said plurality of covers, comprising:

a plurality of shields, each of said plurality of shields having first and second sides, said first side for touching a body of a person, and an adhesive backing on said second side for adhering said shield to said surface area of said diaphragm of said stethoscope so that said shield entirely covers said surface area of said diaphragm; and a dispensing container for holding said plurality of shields, said adhesive backing on one of said plurality of shields being detachably connected with an adjacent, underlying one of said plurality of shields.

10. The combination as recited in claim 9, each of said plurality of shields further having a shield portion and a pull-tab or a flap extending from said shield portion, wherein said one of said plurality of shields is detachably connected with said pull-tab or said flap on said adjacent, underlying one of said plurality of shields.

* * * * *